United States Patent
Truckai et al.

(10) Patent No.: US 6,802,843 B2
(45) Date of Patent: Oct. 12, 2004

(54) ELECTROSURGICAL WORKING END WITH RESISTIVE GRADIENT ELECTRODES

(76) Inventors: Csaba Truckai, 19566 Arden Ct., Saratoga, CA (US) 95070; John H. Shadduck, 1490 Vistazo W., Tiburon, CA (US) 94920

(*) Notice: Subject to any disclaimer, the term of this patent is extended or adjusted under 35 U.S.C. 154(b) by 87 days.

(21) Appl. No.: 10/241,874

(22) Filed: Sep. 12, 2002

(65) Prior Publication Data

US 2003/0069579 A1 Apr. 10, 2003

Related U.S. Application Data

(60) Provisional application No. 60/322,200, filed on Sep. 13, 2001.

(51) Int. Cl.[7] .............................................. A61B 18/18
(52) U.S. Cl. .......................................... 606/51; 606/50
(58) Field of Search ............................. 606/41, 49, 50, 606/61, 52

(56) References Cited

U.S. PATENT DOCUMENTS

| | | |
|---|---|---|
| 659,409 A | 10/1900 | Mosher |
| 1,586,645 A | 6/1926 | Bierman |
| 1,798,902 A | 3/1931 | Raney |
| 1,881,250 A | 10/1932 | Tomlinson |
| 2,031,682 A | 2/1936 | Wappler et al. |
| 3,651,811 A | 3/1972 | Hildebrandt et al. |
| 3,685,518 A | 8/1972 | Beuerle et al. |
| 3,730,188 A | 5/1973 | Ellman |
| 3,768,482 A | 10/1973 | Shaw |
| 3,826,263 A | 7/1974 | Cage et al. |
| 4,092,986 A | 6/1978 | Schneiderman |
| 4,198,957 A | 4/1980 | Cage et al. |
| 4,219,025 A | 8/1980 | Johnson |
| 4,231,371 A | 11/1980 | Lipp |
| 4,232,676 A | 11/1980 | Herczog |

(List continued on next page.)

FOREIGN PATENT DOCUMENTS

| | | |
|---|---|---|
| EP | 341 446 A2 | 4/1989 |
| EP | 517 244 B1 | 3/1996 |
| EP | 518 230 B1 | 5/1996 |
| FR | 2536924 A1 | 6/1984 |
| FR | 2647683 A1 | 12/1990 |
| GB | 2037167 A | 7/1980 |
| GB | 2066104 A | 7/1981 |
| GB | 2133290 A | 7/1984 |
| GB | 2161082 A | 1/1986 |
| SU | 342617 | 10/1977 |
| WO | WO 93/08754 A1 | 5/1993 |
| WO | WO 94/24949 A1 | 11/1994 |
| WO | WO 94/24951 A1 | 11/1994 |

OTHER PUBLICATIONS

Corson, S.L., "Two new laparoscopic instruments: Bipolar sterilizing forceps and uterine manipulator," *Medical Instrumentation*, 11(1):7–8 (1977).

(List continued on next page.)

*Primary Examiner*—Roy D. Gibson
(74) *Attorney, Agent, or Firm*—Townsend and Townsend and Crew LLP

(57) ABSTRACT

An electrosurgical working end and method for transecting an anatomic structure along a targeted line and for creating a thermal welds along either of both transected tissue margins, for example for use in a partial lung resection procedure. In one embodiment, the working end provides elongate curved or linear guide members that can be positioned on opposing sides of the targeted anatomic structure. The working end carries a slidable member with interior channels that receive the guide or jaw members. The electrode or electrodes carried by of working end define a resistive gradient for creating controlled Rf ohmic heating in the engaged tissue.

18 Claims, 18 Drawing Sheets

U.S. PATENT DOCUMENTS

| | | |
|---|---|---|
| 4,271,838 A | 6/1981 | Lasner et al. |
| 4,353,371 A | 10/1982 | Cosman |
| 4,370,980 A | 2/1983 | Lottick |
| 4,375,218 A | 3/1983 | DiGeronimo |
| 4,492,231 A | 1/1985 | Auth |
| 4,590,934 A | 5/1986 | Malis et al. |
| 4,608,981 A | 9/1986 | Rothfuss et al. |
| 4,633,874 A | 1/1987 | Chow et al. |
| 4,655,216 A | 4/1987 | Tischer |
| 4,671,274 A | 6/1987 | Sorochenko |
| 4,691,703 A | 9/1987 | Auth et al. |
| 4,763,669 A | 8/1988 | Jaeger |
| 4,785,807 A | 11/1988 | Blanch |
| 4,848,337 A | 7/1989 | Shaw et al. |
| 4,850,353 A | 7/1989 | Stasz et al. |
| 4,887,612 A | 12/1989 | Esser et al. |
| 4,940,468 A | 7/1990 | Petillo |
| 4,958,539 A | 9/1990 | Stasz et al. |
| 4,969,885 A | 11/1990 | Farin |
| 4,985,030 A | 1/1991 | Melzer et al. |
| 5,009,656 A | 4/1991 | Reimels |
| 5,057,106 A | 10/1991 | Kasevich et al. |
| 5,057,107 A | 10/1991 | Parins et al. |
| 5,085,659 A | 2/1992 | Rydell |
| 5,104,025 A | 4/1992 | Main et al. |
| 5,122,137 A | 6/1992 | Lennox |
| 5,147,356 A | 9/1992 | Bhatta |
| 5,147,357 A | 9/1992 | Rose et al. |
| 5,151,102 A | 9/1992 | Kamiyama et al. |
| 5,190,541 A | 3/1993 | Abele et al. |
| 5,201,900 A | 4/1993 | Nardella |
| 5,207,691 A | 5/1993 | Nardella |
| 5,258,006 A | 11/1993 | Rydell et al. |
| 5,267,998 A | 12/1993 | Hagen |
| 5,269,780 A | 12/1993 | Roos |
| 5,290,286 A | 3/1994 | Parins |
| 5,306,280 A | 4/1994 | Bregen et al. |
| 5,308,311 A | 5/1994 | Eggers et al. |
| 5,324,289 A | 6/1994 | Eggers |
| 5,336,221 A | 8/1994 | Anderson |
| 5,360,428 A | 11/1994 | Hutchinson, Jr. |
| 5,364,389 A | 11/1994 | Anderson |
| 5,389,098 A | 2/1995 | Tsuruta et al. |
| 5,403,312 A | 4/1995 | Yates et al. |
| 5,417,687 A | 5/1995 | Nardella et al. |
| 5,443,463 A | 8/1995 | Stern et al. |
| 5,445,638 A | 8/1995 | Rydell et al. |
| 5,451,224 A | 9/1995 | Goble et al. |
| 5,458,598 A | 10/1995 | Feinberg et al. |
| 5,480,397 A | 1/1996 | Eggers et al. |
| 5,480,398 A | 1/1996 | Eggers |
| 5,507,106 A | 4/1996 | Fox |
| 5,531,744 A | 7/1996 | Nardella et al. |
| 5,571,153 A | 11/1996 | Wallsten |
| 5,573,535 A | 11/1996 | Viklund |
| 5,593,406 A | 1/1997 | Eggers et al. |
| 5,611,798 A | 3/1997 | Eggers |
| 5,624,452 A | 4/1997 | Yates |
| 5,674,220 A | 10/1997 | Fox et al. |
| 5,693,051 A | 12/1997 | Schulze et al. |
| 5,716,366 A | 2/1998 | Yates |
| 5,735,848 A | 4/1998 | Yates et al. |
| 5,755,717 A | 5/1998 | Yates et al. |
| 5,766,166 A | 6/1998 | Hooven |
| 5,776,130 A | 7/1998 | Buysse et al. |
| 5,797,938 A | 8/1998 | Paraschac et al. |
| 5,800,449 A | 9/1998 | Wales |
| 5,807,392 A | 9/1998 | Eggers |
| 5,833,690 A | 11/1998 | Yates et al. |
| 5,911,719 A | 6/1999 | Eggers |
| 5,947,984 A | 9/1999 | Whipple |
| 6,019,758 A | 2/2000 | Slater |
| 6,039,733 A | 3/2000 | Buysse et al. |
| 6,074,389 A | 6/2000 | Levine et al. |
| 6,086,586 A | 7/2000 | Hooven |
| 6,113,598 A | 9/2000 | Baker |
| 6,132,429 A * | 10/2000 | Baker .......................... 606/50 |
| 6,139,508 A | 10/2000 | Simpson et al. |
| 6,152,923 A | 11/2000 | Ryan |
| 6,162,220 A | 12/2000 | Nezhat |
| 6,174,309 B1 | 1/2001 | Wrublewski et al. |
| 6,176,857 B1 | 1/2001 | Ashley |
| 6,179,834 B1 | 1/2001 | Buysse et al. |
| 6,179,835 B1 | 1/2001 | Panescu et al. |
| 6,179,837 B1 | 1/2001 | Hooven |
| 6,187,003 B1 | 2/2001 | Buysse et al. |
| 6,190,386 B1 | 2/2001 | Rydell |
| 6,193,709 B1 | 2/2001 | Miyawaki et al. |
| 6,270,497 B1 | 8/2001 | Sekino et al. |
| 6,273,887 B1 | 8/2001 | Yamauchi et al. |
| 6,277,117 B1 | 8/2001 | Tetzlaff et al. |
| 6,296,640 B1 | 10/2001 | Wampler et al. |
| 6,328,703 B1 | 12/2001 | Murakami |
| 6,334,861 B1 | 1/2002 | Chandler et al. |
| 6,350,264 B1 | 2/2002 | Hooven |
| 6,352,536 B1 | 3/2002 | Buysse et al. |
| 6,398,779 B1 | 6/2002 | Buysse et al. |
| 6,409,725 B1 | 6/2002 | Khandkar et al. |
| 6,451,018 B1 | 9/2002 | Lands et al. |
| 6,458,128 B1 | 10/2002 | Schulze |
| 6,458,130 B1 | 10/2002 | Frazier et al. |
| 6,464,704 B2 | 10/2002 | Schmaltz et al. |
| 6,468,275 B1 | 10/2002 | Wampler et al. |
| 6,500,176 B1 | 12/2002 | Truckai et al. |
| 6,511,480 B1 | 1/2003 | Tetzlaff et al. |
| 6,527,767 B2 | 3/2003 | Wang et al. |
| 6,533,778 B2 * | 3/2003 | Herzon ........................ 606/28 |
| 6,533,784 B2 | 3/2003 | Truckai et al. |
| 6,554,829 B2 | 4/2003 | Schulze et al. |
| 6,575,968 B1 | 6/2003 | Eggers et al. |
| 6,585,735 B1 | 7/2003 | Lands et al. |
| 6,632,193 B1 | 10/2003 | Davison et al. |
| 6,652,521 B2 | 11/2003 | Schulze |
| 2002/0052599 A1 | 5/2002 | Goble |
| 2002/0115997 A1 | 8/2002 | Truckai et al. |
| 2002/0120266 A1 | 8/2002 | Truckai et al. |
| 2002/0169392 A1 | 11/2002 | Truckai et al. |
| 2002/0177848 A1 | 11/2002 | Truckai et al. |
| 2003/0018327 A1 | 1/2003 | Truckai et al. |
| 2003/0050635 A1 | 3/2003 | Truckai et al. |
| 2003/0055417 A1 | 3/2003 | Truckai et al. |
| 2003/0069579 A1 | 4/2003 | Truckai et al. |
| 2003/0078573 A1 | 4/2003 | Truckai et al. |
| 2003/0078577 A1 | 4/2003 | Truckai et al. |
| 2003/0078578 A1 | 4/2003 | Truckai et al. |
| 2003/0114851 A1 | 6/2003 | Truckai et al. |
| 2003/0125727 A1 | 7/2003 | Truckai et al. |
| 2003/0139741 A1 | 7/2003 | Goble et al. |
| 2003/0144652 A1 | 7/2003 | Baker et al. |

OTHER PUBLICATIONS

Burton, J.D.K., "New Inventions," *The Lancet*, pp. 650–651 (1959).

Nardella, P.C., "Radio Frequency Energy and Impedance Feedback," *Proc. SPIE. Catheter–Based Sensing and Imaging Technology*, 1068: 42–48 (1989).

Vallfors et al., "Automatically controlled bipolar electrocoagulation—'COA–COMP'," *Neurosurg Rev.*, 187–190 (1984).

* cited by examiner

US 6,802,843 B2

ELECTROSURGICAL WORKING END WITH RESISTIVE GRADIENT ELECTRODES

CROSS-REFERENCE TO RELATED APPLICATIONS

This application claims benefit of Provisional U.S. Patent Application Ser. No. 60/322,200 filed Sep. 13, 2001 having the same title as this disclosure, which is incorporated herein by reference.

BACKGROUND OF THE INVENTION

1. Field of the Invention

This invention relates to medical devices and more particularly relates to the working end of an electrosurgical instrument that is adapted for sealing or welding tissue that is engaged between paired jaw members. More specifically, the elongate jaw members carry electrodes with engagement surfaces that provide a resistive gradient for causing controlled heating of engaged tissue.

2. Description of the Related Art

In various open and laparoscopic surgeries, it is necessary to weld or seal the margins of transected tissue volumes, for example, in a lung resection. In some procedures, stapling instruments are used to apply a series of mechanically deformable staples to seal the transected edge a tissue volume. Such mechanical devices may create a seal that leaks which can result in later complications.

Various radiofrequency (Rf) surgical instruments have been developed for sealing the edges of transected tissues. For example, FIG. 1A shows a sectional view of paired electrode-jaws 2a and 2b of a typical prior art bi-polar Rf grasper grasping two tissue layers. In a typical bi-polar jaw arrangement, each jaw face comprises an electrode and Rf current flows across the tissue between the first and second polarities in the opposing jaws that engage opposing exterior surfaces of the tissue. FIG. 1A shows typical lines of bi-polar current flow between the jaws. Each jaw in FIG. 1A has a central slot adapted to receive a reciprocating blade member as is known in the art for transecting the captured vessel after it is sealed.

While bi-polar graspers as in FIG. 1A can adequately seal or weld tissue volumes that have a small cross-section, such bi-polar instruments are often ineffective in sealing or welding many types of anatomic structures, e.g., (i) anatomic structures having walls with irregular or thick fibrous content, such as lung tissue; (ii) bundles of disparate anatomic structures, (iii) substantially thick anatomic and structures, and (iv) large diameter blood vessels having walls with thick fascia layers.

As depicted in FIG. 1A, a prior art grasper-type instrument is depicted with jaw-electrodes engaging opposing side of a tissue volume with substantially thick, dense and non-uniform fascia layers underlying its exterior surface, for example, a large diameter blood vessel. As depicted in FIG. 1A, the fascia layers f prevent a uniform flow of current from the first exterior tissue surface s to the second exterior tissue surface s that are in contact with electrodes 2a and 2b. The lack of uniform bi-polar current across the fascia layers f causes non-uniform thermal effects that typically result in localized tissue desiccation and charring indicated at c. Such tissue charring can elevate impedance levels in the captured tissue so that current flow across the tissue is terminated altogether. FIG. 1B depicts an exemplary result of attempting to create a weld across tissue with thick fascia layers f with a prior art bi-polar instrument. FIGS. 1A–1B show localized surface charring c and non-uniform weld regions w in the medial layers m of vessel. Further, FIG. 1B depicts a common undesirable characteristic of prior art welding wherein thermal effects propagate laterally from the targeted tissue causing unwanted collateral (thermal) damage indicated at d.

What is needed is an instrument working end that can utilize Rf energy in new delivery modalities: (i) to weld or seal tissue volumes that are not uniform in hydration, density and collagenous content; (ii) to weld a targeted tissue region while substantially preventing collateral thermal damage in regions lateral to the targeted tissue; (iii) to weld a transected margin of a bundle of disparate anatomic structures; and (iv) to weld a transected margin of a substantially thick anatomic structure.

SUMMARY OF THE INVENTION

The object of the present invention is to provide an instrument and working end that is capable of transecting tissue and highly compressing tissue to allow for controlled Rf energy delivery to the transected tissue margins. The objective of the invention is to effectively weld tissues that have thick fascia layers or other layers with non-uniform fibrous content. Such tissues are difficult to seal since the fascia layers can prevent uniform current flow and uniform ohmic heating of the tissue.

As background, the biological mechanisms underlying tissue fusion by means of thermal effects are not fully understood. In general, the delivery of Rf energy to a captured tissue volume elevates the tissue temperature and thereby at least partially denatures proteins in the tissue. One objective is to denature such proteins, including collagen, into a proteinaceous amalgam that intermixes and fuses together as the proteins renature. As the treated region heals over time, the so-called weld is reabsorbed by the body's wound healing process.

In order to create an effective weld in a tissue volume dominated by the fascia layers, it has been found that several factors are critical. It is necessary to create a substantially even temperature distribution across the targeted tissue volume to create a uniform weld or seal. Fibrous tissue layers (i.e., fascia) conduct Rf current differently than adjacent less-fibrous layers, and it is believed that differences in extracellular fluid content in such adjacent tissues also contribute greatly to the differences in ohmic heating. It has been found that by applying very high compressive forces to fascia layers and underlying non-fibrous layers, the extracellular fluids migrate from the site to collateral regions. Thus, the compressive forces can make resistance more uniform regionally within the engaged tissue.

Another aspect of the invention provides means for creating high compression forces over a very elongate working end that engages the targeted tissue. This is accomplished by providing a slidable extension member that defines channels therein that engage the entire length of elongate guide members that guide the extension member over the tissue. The extension member of the invention thus is adapted to provide multiple novel functionality: (i) to transect the tissue, and (ii) contemporaneously to engage the transected tissue margins under high compression within the components of the working end. Optionally, the extension member can be adapted to carry spaced apart longitudinal electrode surfaces for delivery of Rf current to each transected tissue margin from the just-transected medial tissue layers to surface layers.

Of particular interest, the invention further provides first and second jaw engagement surfaces with electrodes that define stepped resistive gradients across the electrodes' engagement surfaces for controlling Rf energy delivery to the engaged tissue. It has been found that precise control of ohmic heating in the engaged tissue can be accomplished by having electrode surfaces that define a plurality of portions with differential resistance to electrical current flow therethrough.

In another embodiment of the invention, the working end includes components of a sensor system which together with a power controller can control Rf energy delivery during a tissue welding procedure. For example, feedback circuitry for measuring temperatures at one or more temperature sensors in the working end may be provided. Another type of feedback circuitry may be provided for measuring the impedance of tissue engaged between various active electrodes carried by the working end. The power controller may continuously modulate and control Rf delivery in order to achieve (or maintain) a particular parameter such as a particular temperature in tissue, an average of temperatures measured among multiple sensors, a temperature profile (change in energy delivery over time), or a particular impedance level or range.

Additional objects and advantages of the invention will be apparent from the following description, the accompanying drawings and the appended claims.

BRIEF DESCRIPTION OF THE DRAWINGS

FIGS. 4A–4B depicting the positioning of the guide members over a targeted transection path in an anatomic structure, and FIG. 4C depicting the advancement of the extension member over the guide tracks.

DETAILED DESCRIPTION OF THE INVENTION

Figure 1A:
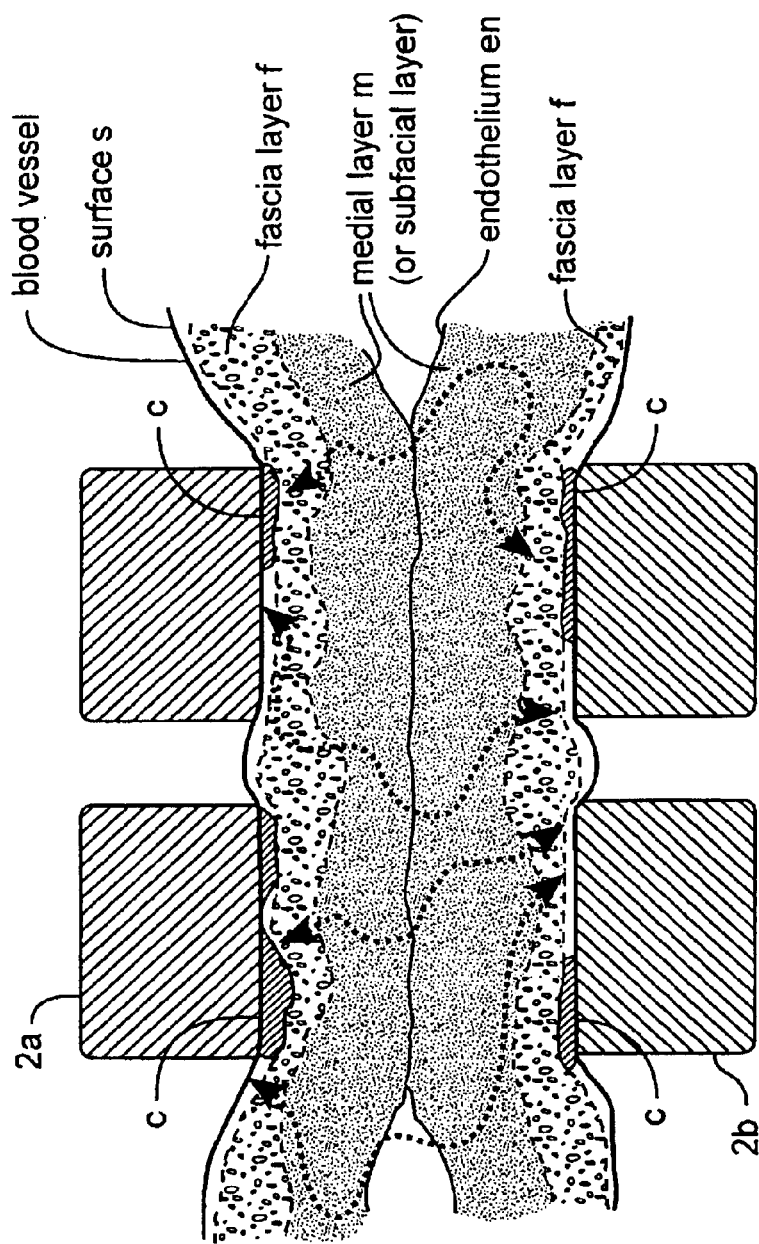
FIG. 1A is an illustration of Rf current flow between the paired jaws of a prior art bi-polar radiofrequency device in a method of sealing a tissue with fascia layers that are resistant to current flow therethrough.
Figure 1B:
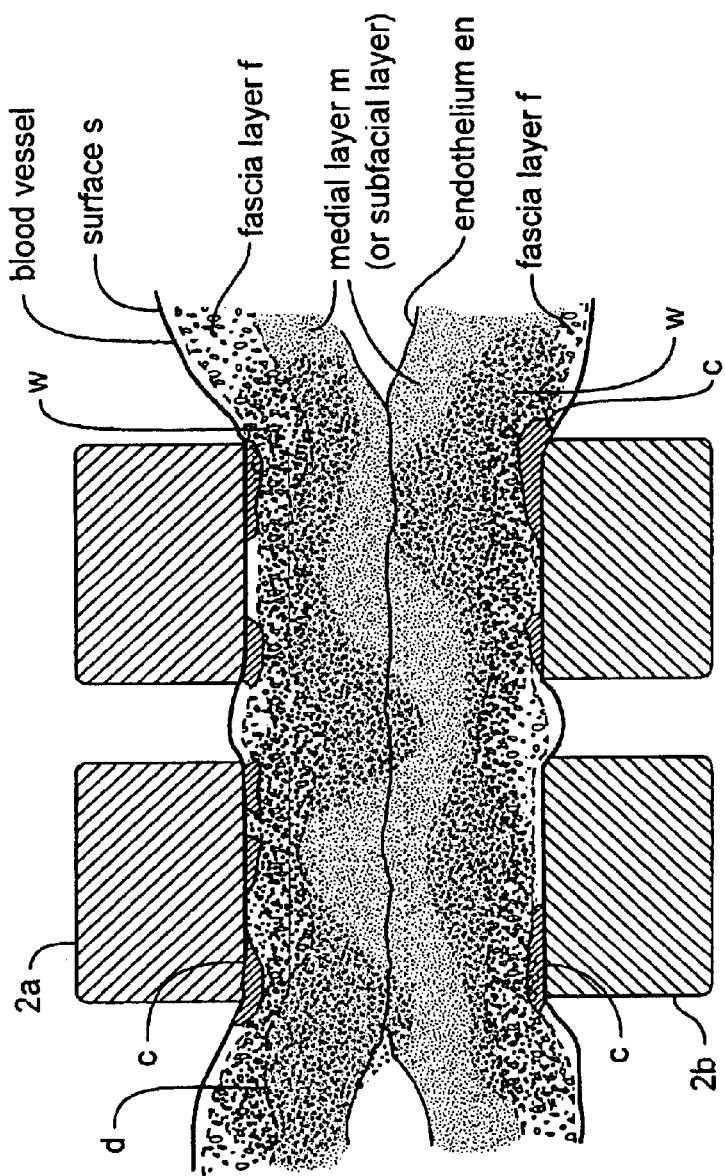
FIG. 1B illustrates representative weld effects of the bi-polar current flow of FIG. 1A.
Figure 2A:
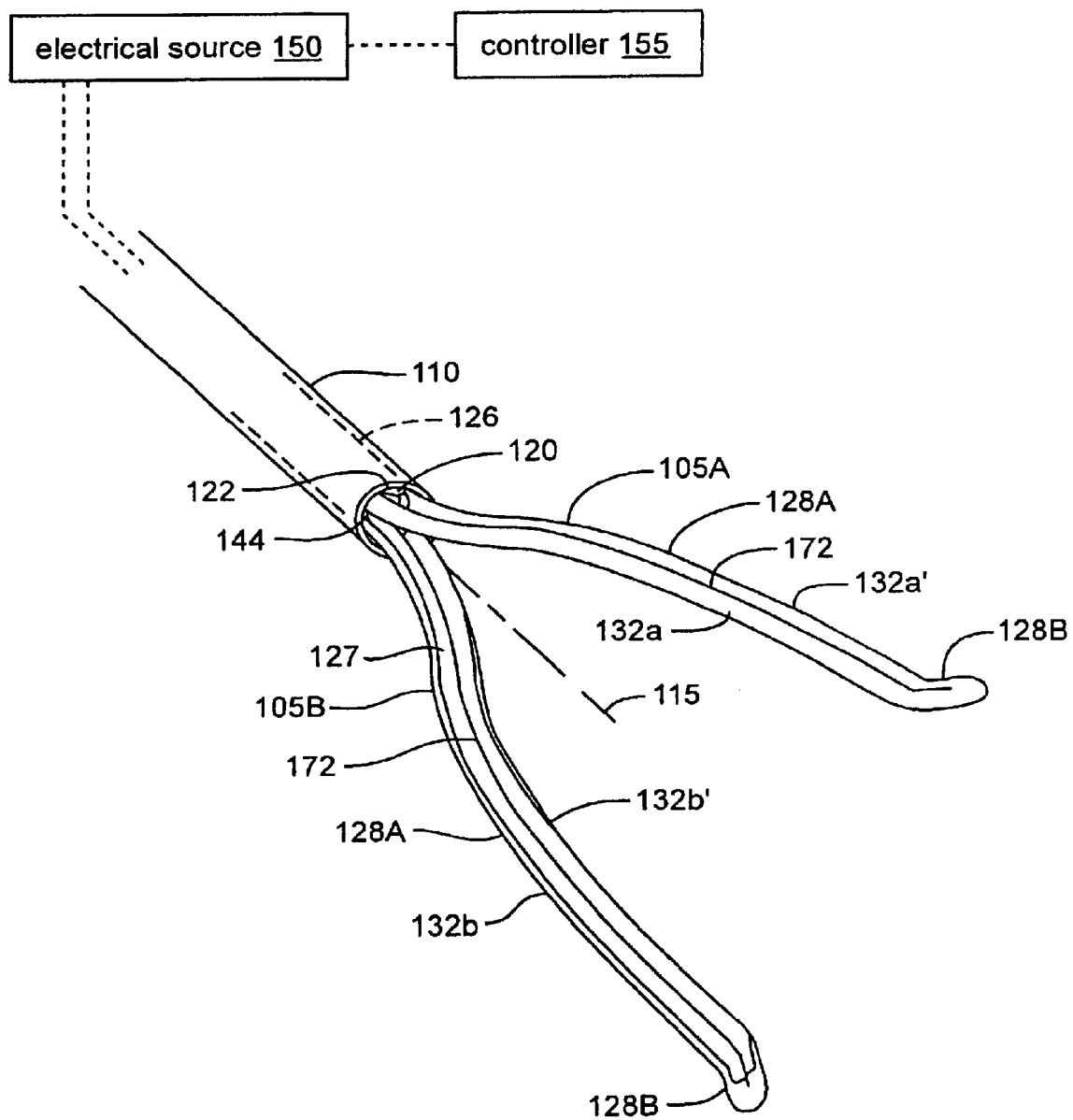
FIG. 2A is a perspective view of a Type "A" working end of the present invention showing first and second guide members extending from the distal end of an introducer, with a cooperating slidable extension member in a retracted position within the introducer.

1. Type "A" Working End for Transecting Tissue and Sealing the Transected Margins. Referring to FIG. 2A, the working end 100 of an exemplary Type "A" embodiment is shown that is adapted for transecting and welding at least one transected tissue margin along a targeted track or path p in tissue, such as lung portion, in an open or endoscopic procedure. The working end 100 has first and second elongate guide members or guide-track members indicated at 105A and 105B that are substantially flexible wire-type elements carried at distal end 108 of an introducer member 110 extending from a proximal handle (not shown). In this Type "A" embodiment, the guide members (or jaws) 105A and 105B extend along a central longitudinal axis 115 and provide multiple functionality: (i) to place over or about a target path p in tissue that is to be transected; (ii) to thereafter guide the terminal portion 118 of an extension member 120 carrying an electrode cutting element 122 along the targeted path p in tissue, and (iii) to provide engagement surfaces 127 for the high-compression engagement of the margins of the transected tissue on both left and right sides of the working end in combination with extension member 120.

In the exemplary embodiment of FIG. 2A, the structural component of introducer portion 110 has a cylindrical cross-section and comprises a thin-wall tubular sleeve (with bore 126) that extends from the proximal handle, although any cross section may be suitable. The diameter of introducer sleeve 110 may range from about 3 mm. to 6 mm., although larger diameter sleeves fall within the scope of the invention. The handle may be any type of pistol-grip or other type of handle known in the art that carries actuator levers or slides to translate the extension member 120 within bore 126 and over the guide tracks 105A and 105B.

Figure 3:
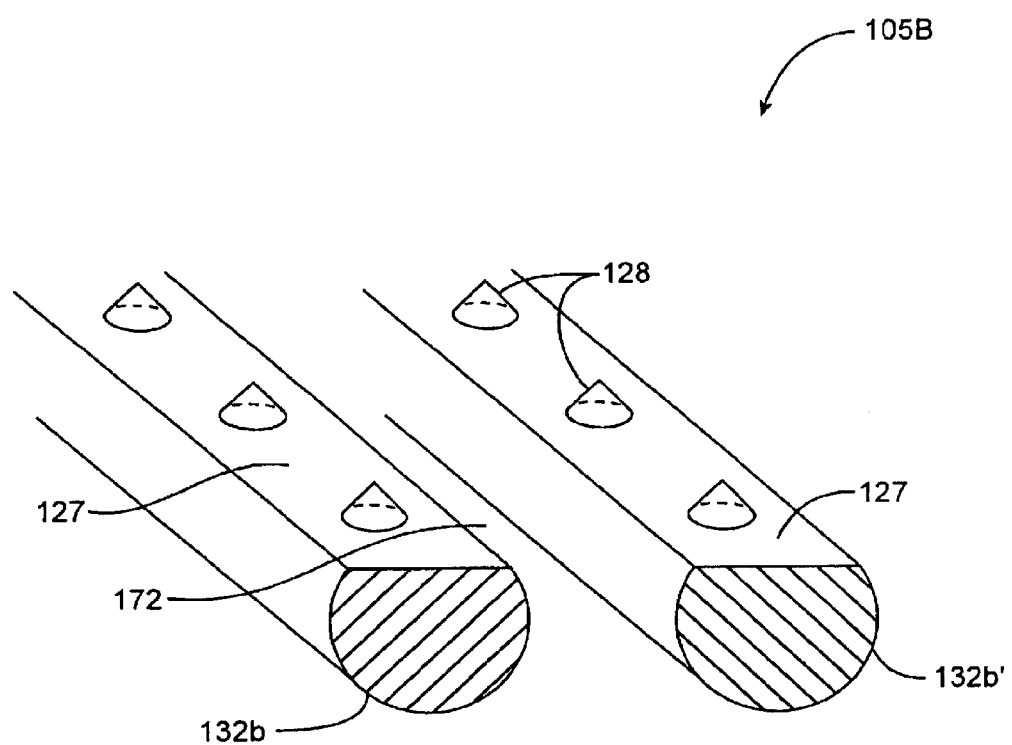
FIG. 3 is sectional view of a guide member of the invention showing exemplary tissue-gripping elements.

As can be seen in FIG. 2A, one embodiment of the working end 100 has very elongate guide members 105A and 105B of a flexible round wire or rod element, for example, having a diameter ranging from about 0.03" to 0.10". The cross-section of guide members 105A and 105B can provide engagement surfaces 127 (collectively) that are flat as shown in FIGS. 2A & 3. Additionally, the surface 127 can carry and type of serrations, sharp projecting elements or any suitable gripping surface better engage tissue as the extension member 120 is advanced over the guides 105A and 105B. FIG. 3 shows exemplary projecting elements 128 (i.e., spikes) that can be provided in the engagement surfaces 127.

Figure 4A:
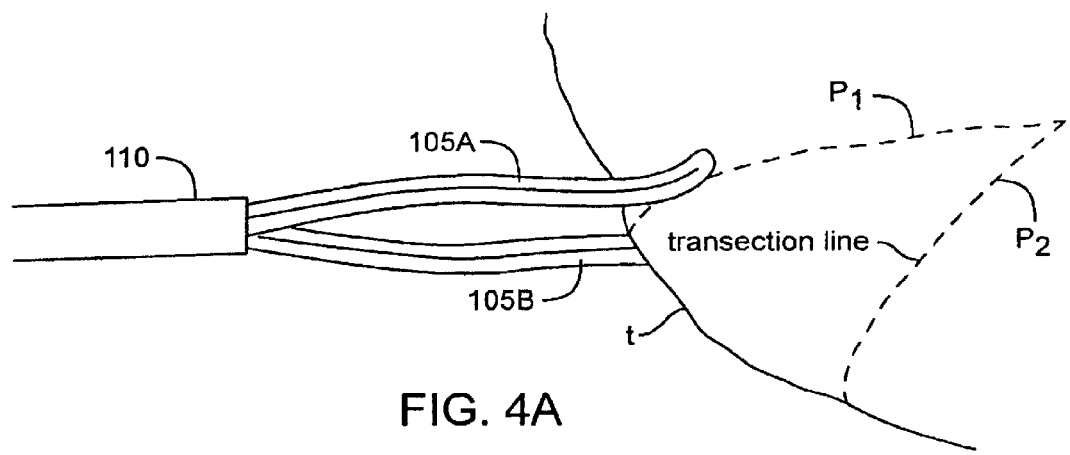
FIGS. 4A–4C are illustrations of initial steps of practicing the method of the invention.
Figure 4B:
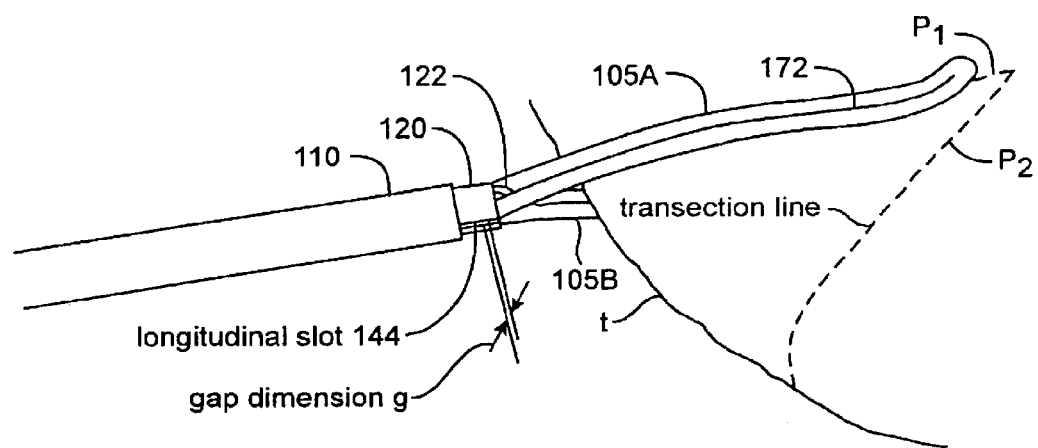
Figure 4C:
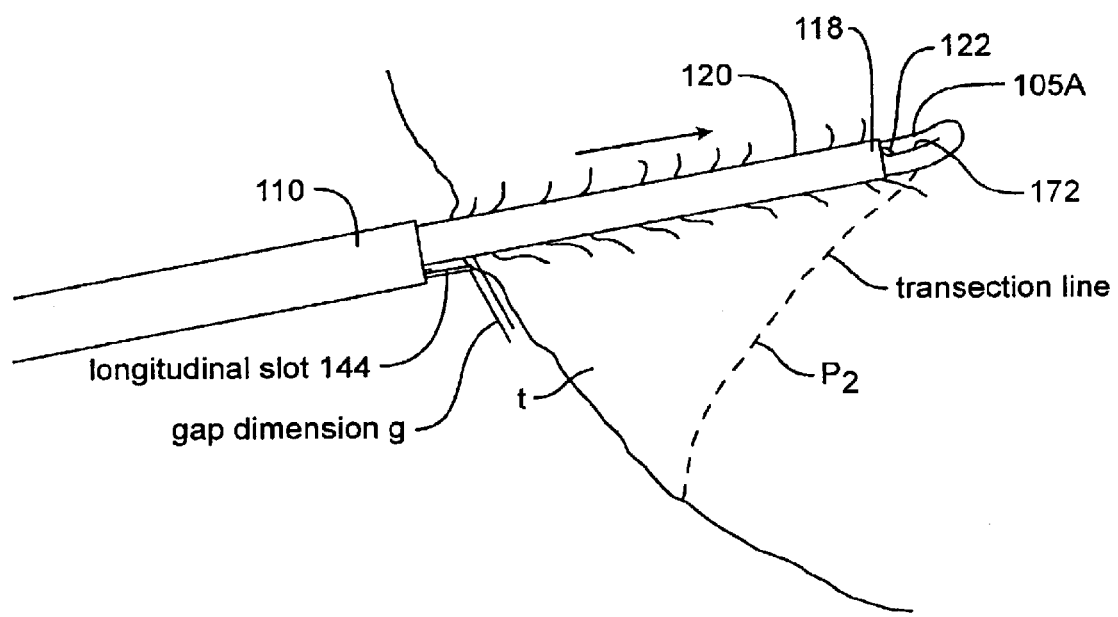

The guide members 105A and 105B in this embodiment define medial outward bowed portions or curve portions indicated at 128A and optional distal angled portions 128B that are adapted to allow guide members 105A and 105B to be pushed over a path p in tissue (see FIG. 4B). It should be appreciated that the shape of the guide members 105A and 105B may be any suitable linear or curved shape to allow ease of placement over a tissue volume targeted for transection. FIGS. 4A–4C illustrate the initial steps of the method of advancing the elongate guide members 105A and 105B over a targeted path in an anatomic structure. FIG. 4A indicates that successive transections along paths $p_1$ and $p_2$ can thus accomplish a wedge resection of a targeted tissue volume while at the same time selectively sealing one or both of the transection margins on either side of each path p.

Figure 2B:
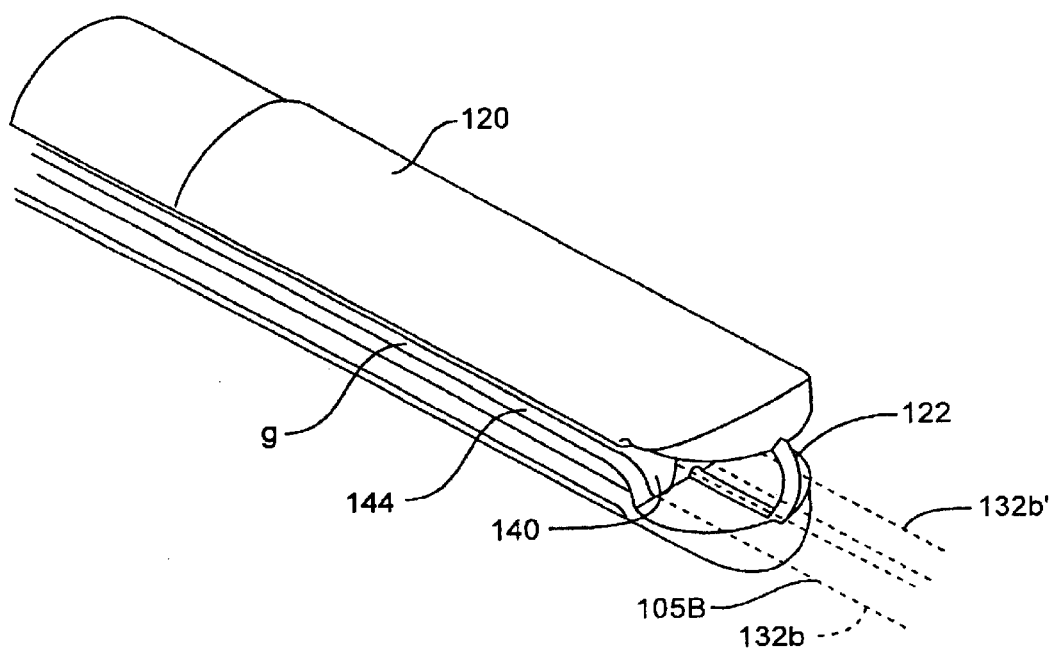
FIG. 2B is perspective view of the distal end of the slidable extension member of FIG. 2A with the lower guide member in phantom view, also showing the distal cutting electrode.
Figure 2C:
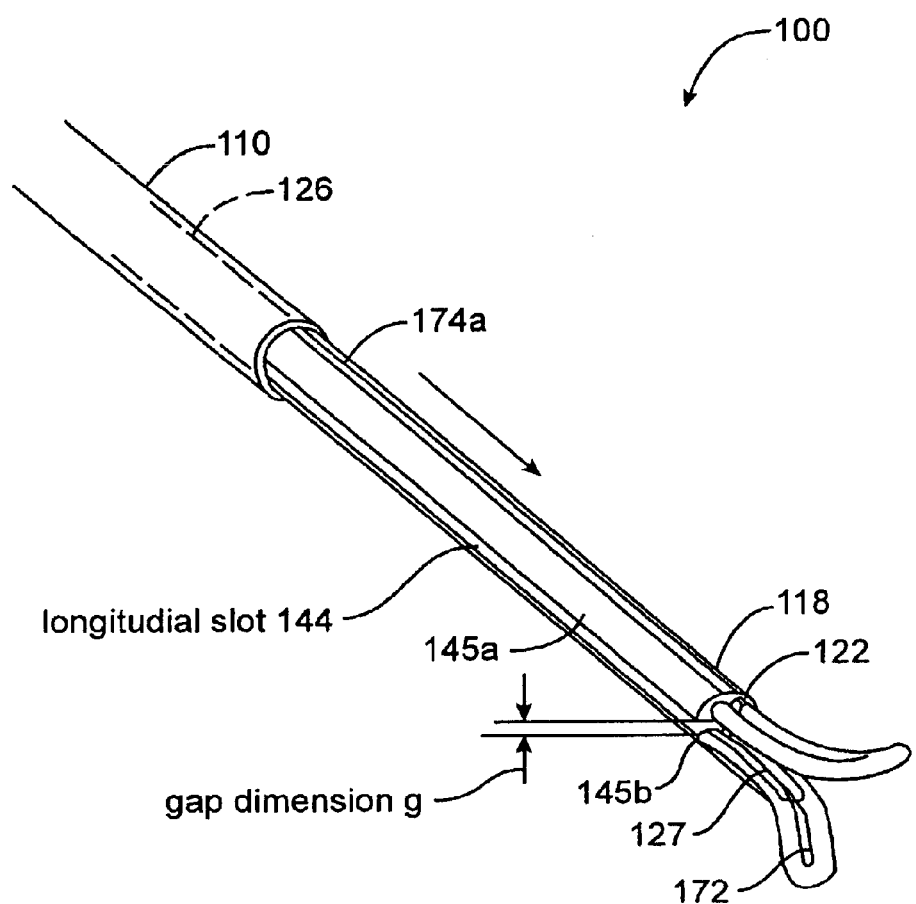
FIG. 2C is another view of the working end of FIG. 2A with the extension member moved toward an extended position over guide members.

FIGS. 2A and 2C illustrate that guide members 105A and 105B preferably are fabricated of a spring-type metal rod formed with suitable curves 128A and 128B. The guide members 105A and 105B do not comprise jaws in the conventional sense since they are substantially flexible and hence lack jaw-type functionality. That is, the guide members 105A and 105B cannot be moved to a closed position to capture tissue as they provide no inherent strength to be moved between such open and closed positions. Rather, the rod-type elements that make up guide members 105A and 105B are adapted only to guide extension member 120 and to serve as a ramp over the tissue to allow the advancement of extension member 120 over the tissue that otherwise would not be possible.

Referring to FIG. 2B, the extension member 120 slides over the rod-type guide elements with its terminal cutting element 122 transecting the tissue, in which process the extension member 120 captures the combination of the transected tissue margins and the guide members 105A and 105B in a high compression sandwich-like arrangement. It has been found that this means of engaging tissue margins is ideally suited for tissue welding with Rf current. In the exemplary embodiment, the rod-like elements of guide members 105A and 105B comprise paired wire elements, for example, indicated as elements or rods 132a and 132a' in guide member 105A and rods 132b and 132b' in guide member 105B (see FIG. 2A). While a metal is a preferred material for guide members 105A and 105B, plastic or composite materials also can be used.

All of the electrosurgical cutting and sealing functionality of the invention is provided in extension member 120 and is described next. As can be seen in FIGS. 2B, 4B–4C and FIG. 5, the extension member 120 has a round exterior cross-section and has a first retracted position within the introducer sleeve 110 (see FIG. 2A). FIGS. 2B & 4C show views of the extension member 120 being advanced toward a second extended position over the guide members 105A and 105B as its distal cutting element 122 in terminal portion 118 transects the captured tissue t.

Figure 5:
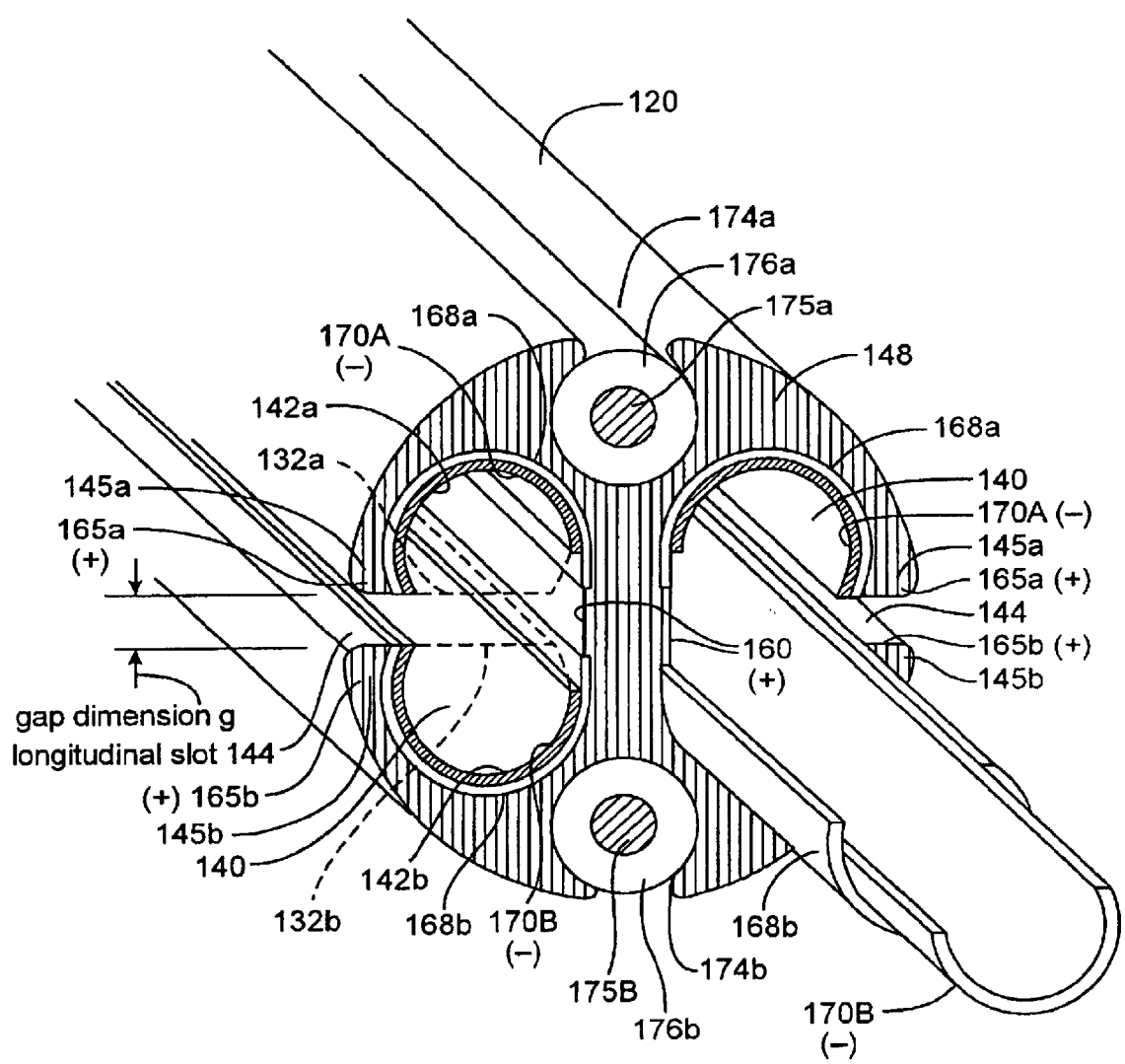
FIG. 5 is an enlarged cross-sectional view of the extension member of FIG. 2B showing the electrode arrangement carried by the extension member.

Now turning to FIGS. 2B, 2C and FIG. 5, the sectional views of extension member 120 show how the various functional components cooperate. In the embodiment depicted in FIGS. 2B and 5, it can be seen that the extension member 120 has left and right channel portions indicated at 140 (collectively) that are shaped to closely fit around the round rod-type elements of guide members 105A and 105B as the member 120 is slidably moved from its first retracted position toward its second extended position.

For example, FIG. 5 shows channel 140 at the right side of the instrument (left in view) that has upper surface portions 142a about its top and side that slidably engage one element (132a) of guide member 105A about exterior surfaces of that round element. Likewise, FIG. 5 shows a lower part of the channel 140 with surface portions 142b about the bottom and side of another element (132b) of the lower guide member 105B that slidably engages an exterior of that element. It thus can be seen how the extension member slides over guide members 105A and 105B and flexes the guide members toward one another to allow the entire assembly to compress very tightly about the opposing surfaces of the captured tissue t as the leading edge electrode 122 transects the tissue. The extension member 120 defines a longitudinal slot 144 that extends from each channel 140 to an exterior of the extension member that receives the tissue margin. The slot 144 of extension member 120 thus defines a predetermined gap dimension indicated at g that comprises a selected dimension to which the captured tissue will be compressed (see FIGS. 4C and 5). The distal end of the gap g (see FIG. 2B) preferably tapers from a more open dimension to a tighter dimension to initially allow the extension member to slide over engaged tissue. The extension member 120 further defines laterally outward portions 145a and 145b above and below slot 144 that engage the tissue margin. It has been found that tissue should be compressed under high forces for effective Rf welding and the gap g can be substantially small for many tissues. It can be appreciated that the extension member in combination with guide members 105A and 105B can apply very high compressive forces over a long path in tissue for purposes of transection that would not possible with a conventional jaw-type instrument.

The extension member 120 depicted in FIG. 5 can be fabricated by in alternative materials (either plastic or metal) by extrusion processes known in the art, or it can be made by various casting methods if made in a conductive metal. One preferred embodiment as depicted in FIG. 5 provides a body 148 of the extension member that is fabricated of any suitable conductive material such as a metal. The proximal end of the extension member 120 is coupled by an electrical lead (not shown) to an electrical source 150 and controller 155. Thus, the extension member 120 carries electrical potential to serve as an electrode body. The body 148 of the extension member has cooperating electrode surface portions 160 and 165a–165b that are exposed to contact the captured tissue: (i) at the transected medial tissue that interfaces the exposed electrode surface indicated at 160, and (ii) at opposed exterior surfaces of the captured tissue that interface the exposed electrode surfaces 165a and 165b at upper and lower portions (145a and 145b) of extension member 120 outboard (laterally outward) of channel 140. For purposes of illustration, these exposed electrode surface portions 160 and 165a–165b are indicated in FIG. 5 to have a positive polarity (+) to cooperate with negative polarity (−) electrodes described next. These opposing polarity electrodes are, of course, spaced apart from one another and coupled to the electrical source 150 that defines the positive and negative polarities during operation of the instrument. In FIG. 5, it should be appreciated that the left and right sides of the extension member are mirror images of one another with reference to their electrode arrangements. Thus, sealing a tissue margin on either side of the extension member is independent of the other—after the targeted tissue is transected and captured for such Rf welding or sealing as in FIG. 4C. For simplicity, this disclosure describes in detail the electrosurgical methods of sealing a transected tissue margin on one side of the extension member, with the understanding that mirror image events also (optionally) occur on the other side of the assembly.

Still referring to FIG. 5, thin insulator layers 168a and 168b of any suitable plastic or ceramic extend in a partial radius around upper and lower portions of channel 140.

Inward of the thin insulator layers 168 are opposing (−) polarity electrodes 170A and 170B that constitute radial sections of elongate hypotubes fitted in the channel and therefore comprise inner surface portions of the channel 140. These longitudinal negative (−) polarity electrodes 170A and 170B, for example of stainless steel, provide the additional advantage of being durable for sliding over the rod elements 132a and 132b that make up portions of guides 105A and 105B. It can be seen that all electrical connections are made to extension member 120 which carries the actual opposing polarity electrodes, thus simplifying fabrication and assembly of the component parts of the working end.

As described above, the distal terminal portion 118 of extension member 120 carries an electrode cutting element indicated at 122 in FIGS. 2B, 4B and 4C. In FIG. 2B, it can be seen that electrode cutting element 122 moves with the longitudinal space 172 between the paired rod-type elements that comprise each guide member 105A and 105B. FIG. 5 shows that grooves 174a and 174b are provided in the extension member 120 to carry electrical leads 175a and 175b to the cutting electrode 122. These electrical leads 175a and 175b are insulated from the body 148 of extension member 120 by insulative coatings indicated at 176a and 176b.

Now turning to FIGS. 4C and 6, the operation and use of the working end 100 of FIG. 2A in performing a method of the invention can be briefly described as follows. FIG. 4C depicts the extension 120 being advanced from a proximal position toward an extended distal position as it ramps over the tissue by advancing over the guide-track members that compress the tissue just ahead of the advancing extension member. The laterally-outward portions 145a and 145b of the extension member thereby slide over and engage the just-transected tissue margins contemporaneous with the cutting element 122 transecting the tissue. By this means, the transected tissue margins are captured under high compression by working end components on either side of the margins. FIG. 5 thus depicts the targeted tissue margins t captured between upper and lower portions of the extension member outward of channels 140. The targeted tissue t may be any soft tissue or anatomic structure of a patient's body. The targeted tissue is shown with a surface or fascia layer indicated at f and medial tissue layers m. While FIGS. 4B–4C depict the tissue being transected by a high voltage Rf cutting element 122, it should be appreciated that the cutting element also can be a blade member.

Figure 6:
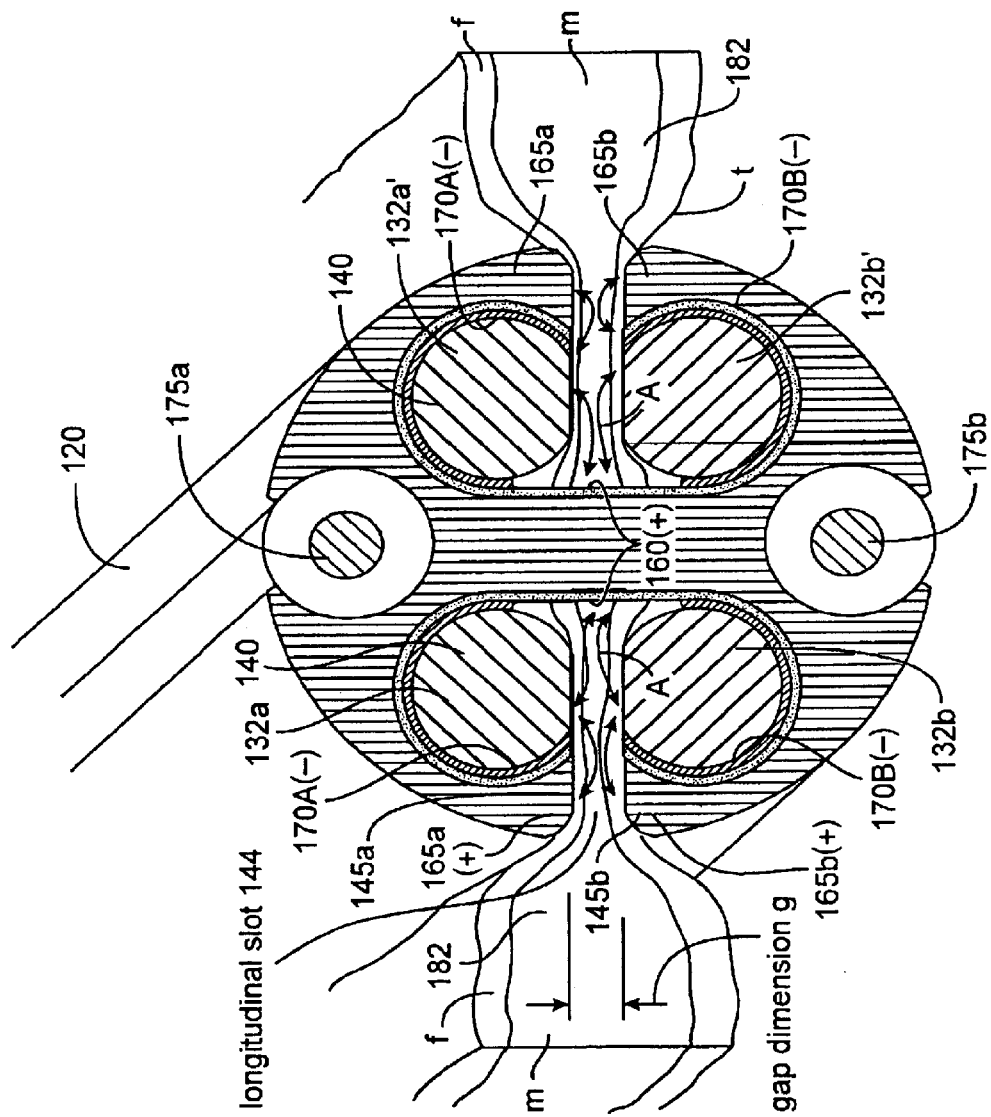
FIG. 6 is a sectional illustration of the extension member of FIG. 5 illustrating the manner of delivering bi-polar Rf current flow to seal or weld a transected tissue margin under high compression.

FIG. 6 provides an illustration of one preferred manner of Rf current flow that causes a sealing or welding effect by the medial-to-surface bi-polar current flow (or vice versa) indicated by arrows A. It has been found that a substantially uniform weld can be created across the captured tissue margin by causing current flow from exposed electrode surfaces 165A and 165B to the electrodes 170A and 170B that further conducts current flow through conductive guide rod elements 132a and 132b. In other words, the sectional illustration of FIG. 6 shows that a weld can be created in the captured tissue margin where proteins (including collagen) are denatured, intermixed under high compressive forces, and fused upon cooling to seal or weld the transected tissue margin. Further, it is believed that the desired weld effects can be accomplished substantially without collateral thermal damage to adjacent tissues indicated at 182 in FIG. 6.

Another embodiment of the invention (not shown) includes a sensor array of individual sensors (or a single sensor) carried in any part of the extension member 120 or guide member 105A–105B that contacts engaged tissue. Such sensors preferably are located either under an electrode 170A–170B or adjacent to an electrode for the purpose of measuring temperatures of the electrode or tissue adjacent to an electrode during a welding procedure. The sensor array typically will consist of thermocouples or thermistors (temperature sensors that have resistances that vary with the temperature level). Thermocouples typically consist of paired dissimilar metals such as copper and constantan which form a T-type thermocouple as is known in the art. Such a sensor system can be linked to feedback circuitry that together with a power controller can control Rf energy delivery during a tissue welding procedure. The feedback circuitry can measure temperatures at one or more sensor locations, or sensors can measure the impedance of tissue, or voltage across the tissue, that is engaged between the electrodes carried by the working end. The power controller then can modulate Rf delivery in order to achieve (or maintain) a particular parameter such as a particular temperature in tissue, an average of temperatures measured among multiple sensors, a temperature profile (change in energy delivery over time), a particular impedance level or range, or a voltage level as is known in the art.

Figure 7:
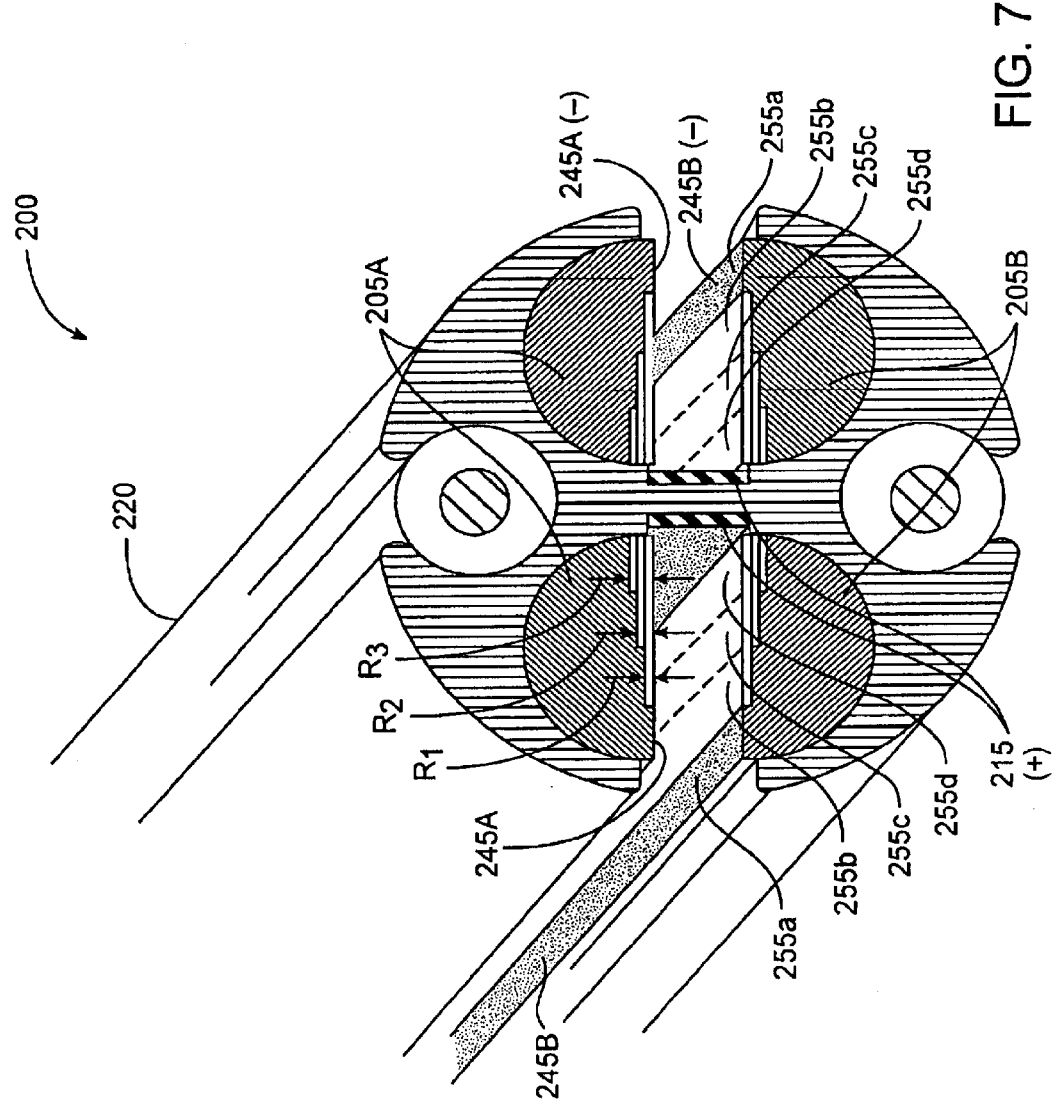
FIG. 7 is a sectional view of a Type "B" working end that open and closes similar to the Type "A" embodiment of FIG. 5, with the Type "B" embodiment providing improved electrode engagement surfaces with a resistive gradient for progressive Rf delivery across an engaged tissue volume.

2. Type "B" Working End for Welding Tissue. FIG. 7 depicts another embodiment of working end 200 in which the guide members or jaws 205A and 205B comprise electrodes of common polarity that cooperate with the opposing polarity central electrode 215 to deliver a bi-polar type of Rf current flow to engaged tissue. In this embodiment, the body of extension member 220 can be of a non-conductive plastic or any metal of composite with an insulative coating. FIG. 7 shows an exemplary embodiment in which extension member 220 does not carry electrical potential to serve as an electrode body, in contrast to the Type "A" embodiment. Still, the extension member 220 carries a central electrode 215 having an exposed surface in each channel 240 that contacts the transected edge the medial tissue layers of the transected tissue that interfaces these electrode surfaces. In use, the Rf current thus will flow between the common-polarity electrode engagement surfaces 245A and 245B of jaws 205A and 205B, respectively, and the opposing polarity central electrode 215.

As described in the Type "A" embodiment, the system again uses extension member 220 that cooperates with guide members 205A and 205B and is thus capable of applying very high compressive forces to tissue t engaged between the engagement surfaces 245A and 245B of the guide members or jaws. The compression forces applied to tissue can be strong enough to greatly reduce the engaged tissue's cross-section. For example, the tissue can be reduced to a selected dimension ranging down to a few thousandths of an inch. It has been found that such high compression is conducive to welding tissue when combined with the manner of Rf current flow through the tissue as previously described.

Of particular interest, the present invention provides further means for allowing precise control of the Rf current paths in the engaged tissue to create more controlled thermal effects-thereby allowing for the creation of a more controlled weld. FIG. 7 shows that the electrode engagement surfaces 245A and 245B (on at least one side of working end 200) define a resistive gradient comprising varied thicknesses of a thin resistive material 250 in adjacent axial-extending portions 255a–255d of the electrode surfaces. It should be appreciated that the jaw surfaces can be serrated for gripping tissue, but for clarity of explanation are shown as smooth in the Figures. More in particular, FIG. 7 shows that differential resistances are provided in the electrode surfaces. FIG. 7 depicts elongate electrode portion 250a in the outer region of each jaw member that is farthest from the opposing polarity central electrode 215. This electrode portion 250a is without a resistive layer or coating. FIG. 7 further shows electrode portion 255b in each jaw member carries a resistive coating having thickness and resistance indicated at $R_1$ wherein the thickness is directly proportional to the level of electrical resistance. In the embodiment of FIG. 7, the next adjacent electrode portion 255c in each jaw has a double-thickness resistive coating having a total thickness (and total resistance) indicated at $R_2$. Similarly, elongate electrode portion 255d in each jaw has a triple-thickness resistive coating having a total thickness and resistance indicated at $R_3$. The resistive coating can be any suitable thin film material (e.g., a resistive metal, ceramic or composite) that is applied in layers by masks of other similar manners known in the art. One manner of creating the gradient electrode surface is to use an electroplating process, combined with masks or the selected removal of layer portions, that provides for deposition of black chrome on the jaw surfaces—a process that has been developed by Seaboard Metal Finishing Co., Inc., 50 Fresh Meadow Rd., West Haven, Conn. 06518. Another suitable manner of creating the resistive gradient electrode surfaces is to use varied thickness layers of a TCX™ coating developed by ThermoCeramix, LLC, 17 Leominster Rd., Shirley, Mass. 01464.

Figure 8A:
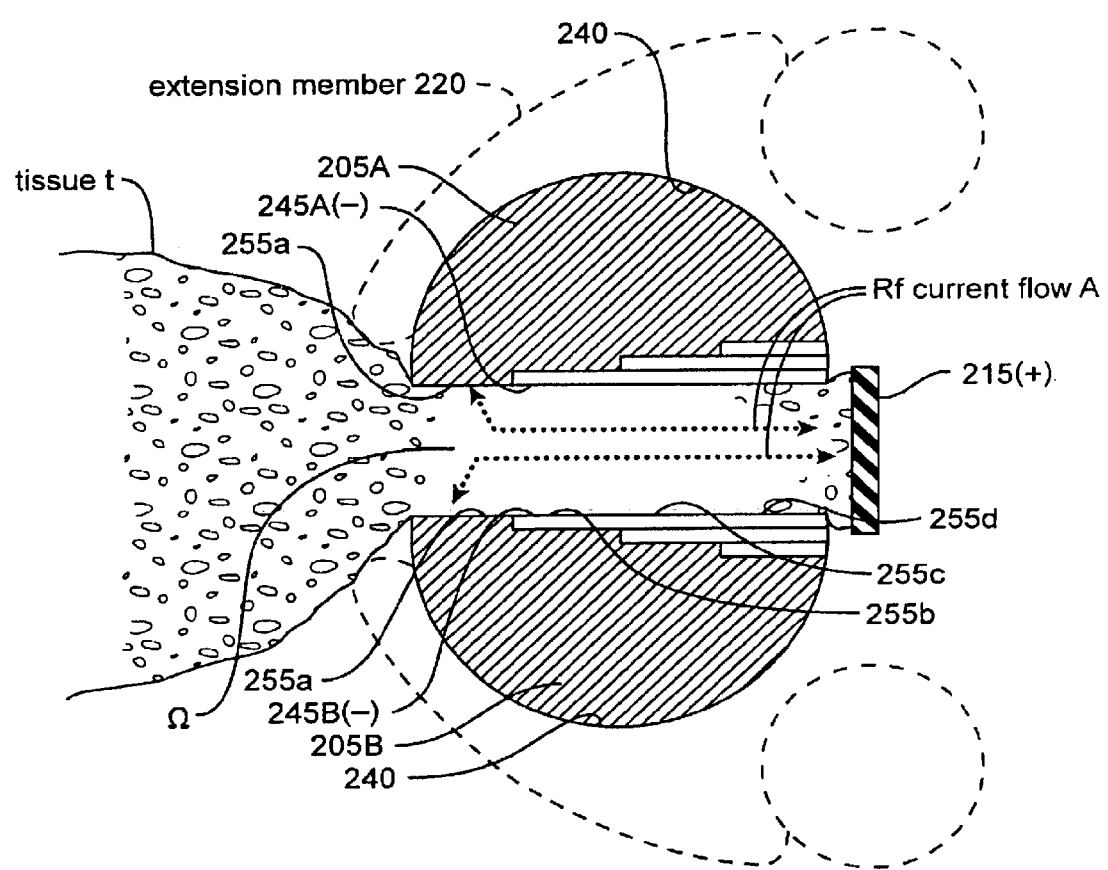
FIGS. 8A–8D are sequential sectional views of the Type "B" working end of FIG. 7 engaging tissue and depicting the induced flow of Rf current progressively through adjacent electrode portions after tissue impedance is altered.

Turning now to FIGS. 8A–8D, the method of the invention in directing Rf current to flow in selected paths of the engaged tissue is shown schematically, following transection of the tissue by the cutting electrode 122 (see FIGS. 2B and 4C). FIG. 8A depicts the initial actuation of controller 155 and electrical source 150 that are coupled to the bi-polar electrode arrangement of the working end 200. In other words, Rf current flow is created between the central electrode 215 (for convenience indicated with (+) polarity) and the common polarity electrode engagement surfaces 245A and 245B (indicated with (−) polarity) of the jaws. In FIG. 8A, it can be understood that the engaged and compressed tissue t has a substantially uniform resistance (indicated at a particular resistance level $\Omega$) to electrical current flow, which resistance $\Omega$ increases substantially as tissue hydration is reduced and the engaged tissue is welded. During the initial activation of energy delivery as depicted in FIG. 8A, Rf current will naturally flow along the lines of least resistance between the bi-polar electrode arrangement. Since, the more inward surface portions (255b–255d) of the electrode engagement surfaces have higher resistivities and thicknesses ($R_1$ to $R_3$), the resistive gradient electrodes will induce or direct the Rf current to flow generally between central electrode 215 and the outermost electrode portions 255a of each jaw as indicated by arrows A in FIG. 8A. The Rf current will flow in this selected manner until the impedance of the tissue volume compressed between electrode portions 255a of each jaw 205A and 205B increases to match or exceed the resistivity $R_1$ of the electrode coating in surface portion 255b.

Figure 8B:
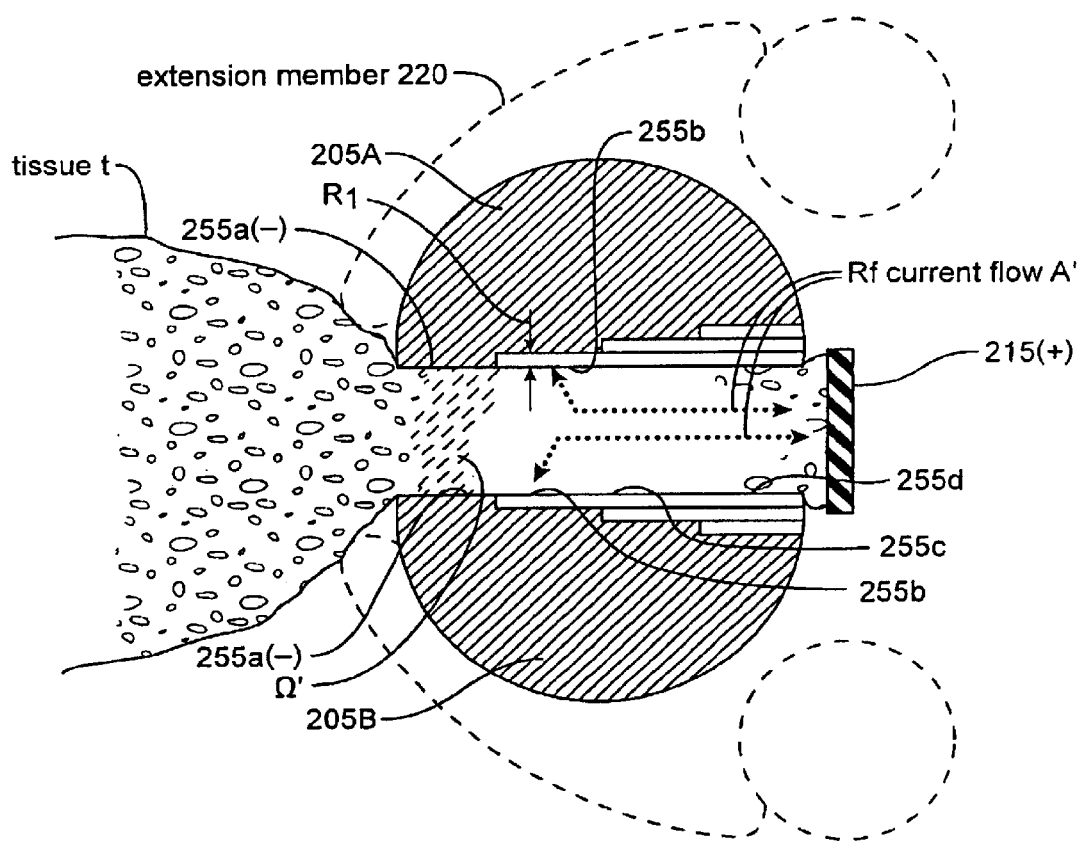
Figure 8C:
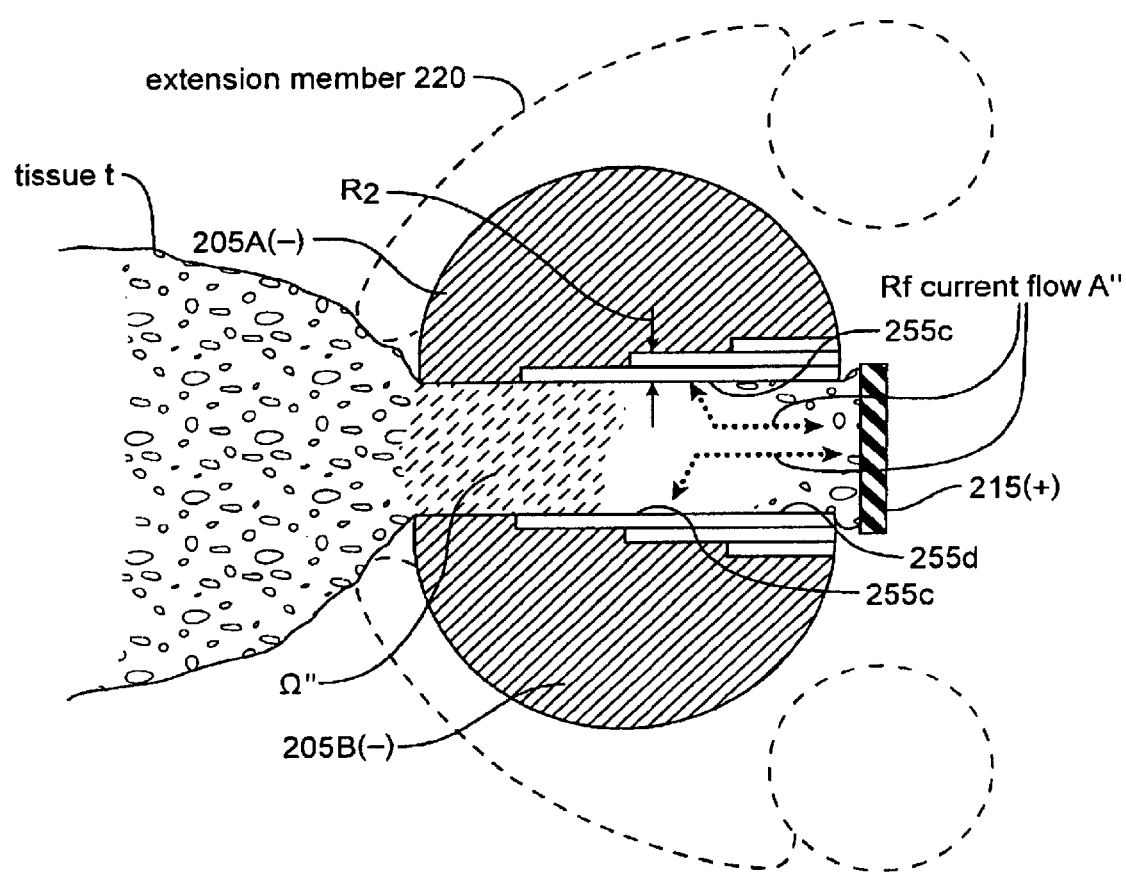
Figure 8D:
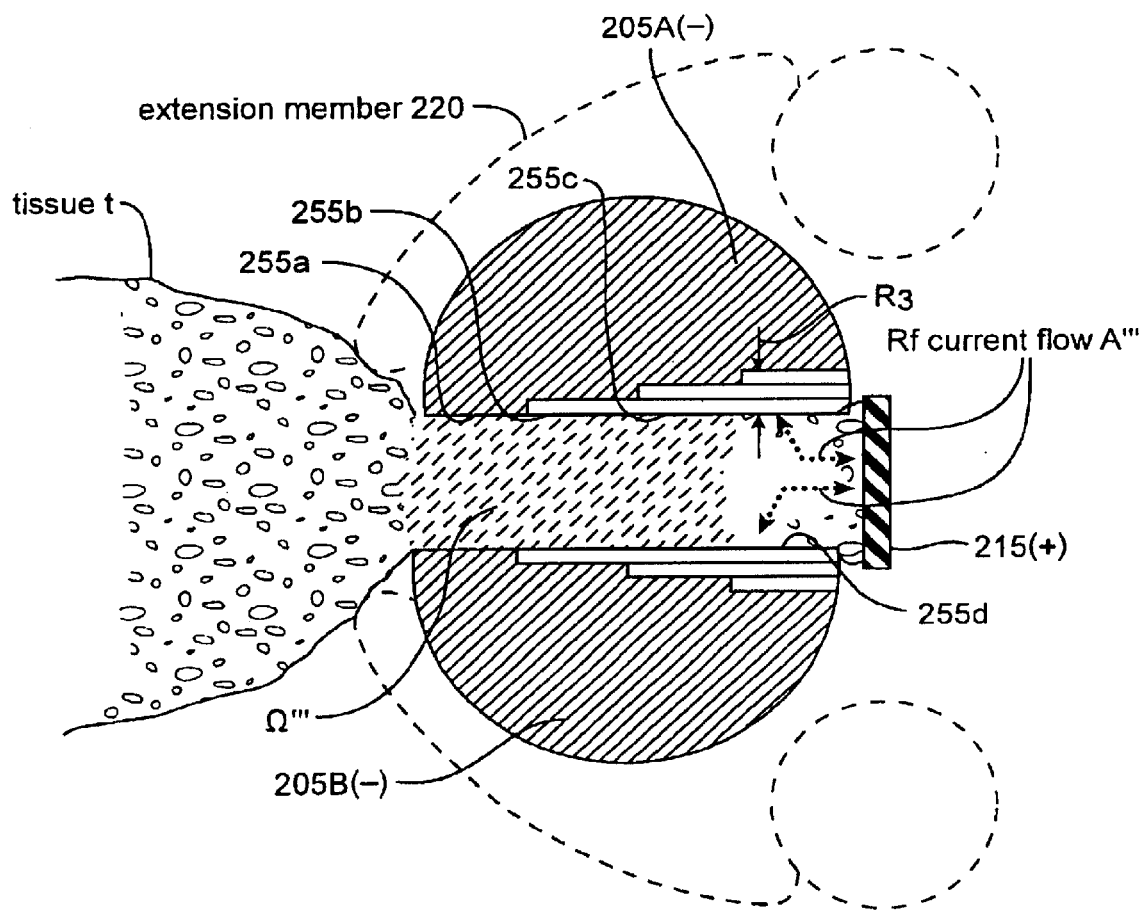

FIG. 8B next illustrates the region of increase tissue resistivity at $\Omega'$ between electrode portions 255a, which then induces or directs Rf flow between the adjacent tissue volume engaged between electrode portions 255b of the opposing jaws as indicated by arrows A' (FIG. 8B). FIG. 8C then illustrates that more outward tissue has its resistance increased, for example to $\Omega''$, with Rf current then induced to flow along a line of lesser resistance through tissue engaged between electrode portions 255c (having resistivity $R_1$) and indicated by arrows A". Finally, FIG. 8D depicts outward tissue with an arbitrary increased resistance $\Omega'''$, with Rf current induced to the tissue engaged between electrode portions 255d (indicated by arrows A''') that is closest to the central electrode 215.

It has been found that the above-described manner of selectively delivering Rf current to tissue can create a uniform thermal effect and biological weld in captured tissue, particularly when the engaged tissue is substantially thin and under high compression. The method of the invention can create a thermally-induced biological weld with little collateral thermal damage in the collateral tissue region indicated at ct.

Figure 9:
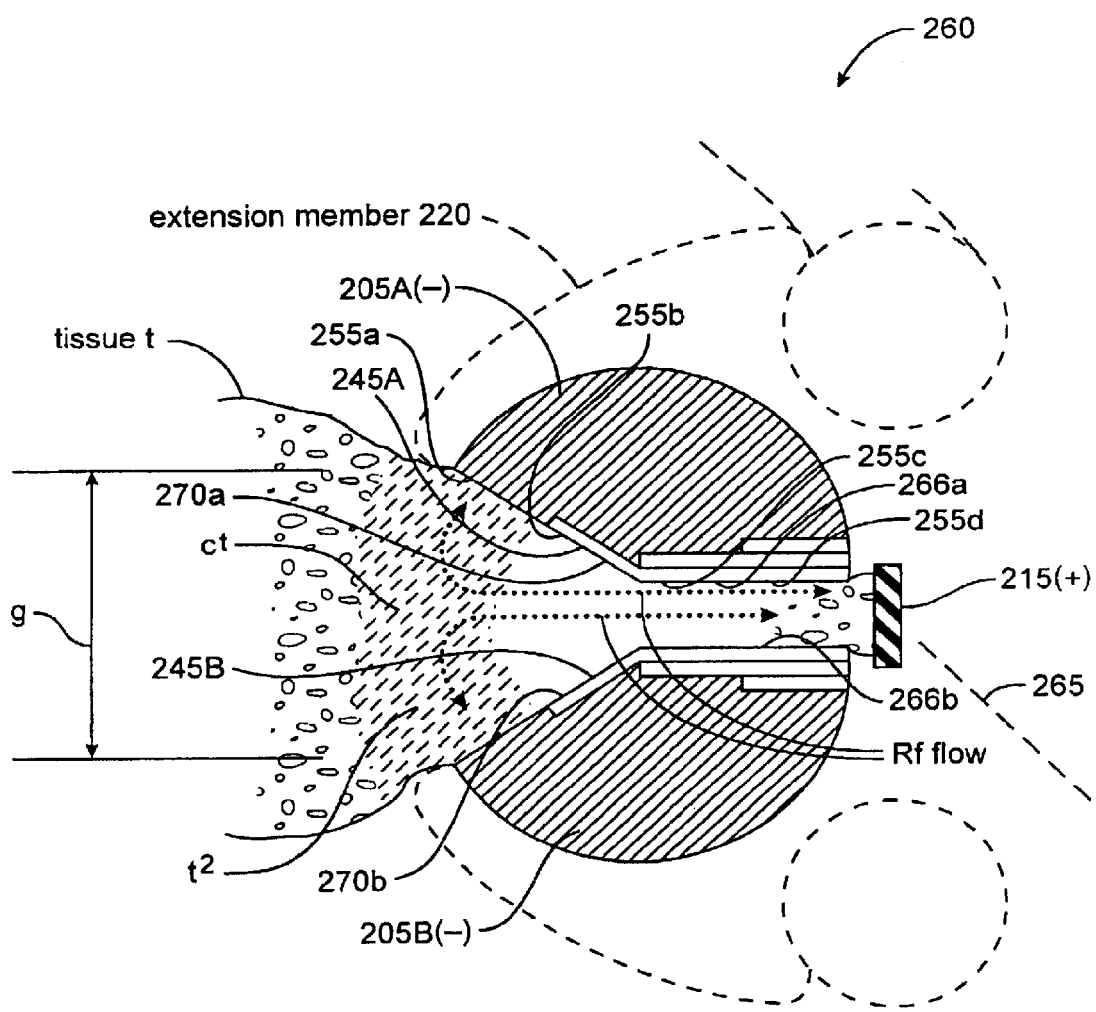
FIG. 9 is a sectional view of an alternative Type "B" working end with gradient electrodes that has non-parallel electrode engagement surfaces for creating a gradual transition between welded tissue and non-welded tissue.

FIG. 9 shows another embodiment of an electrosurgical working end 260 with gradient electrode surfaces 245A and 245B that are adapted for creating a selected dimension coagulation zone or transition zone tz in the engaged tissue between the welded tissue and the more laterally outward tissue that is not elevated in temperature. The previously described embodiment of FIG. 7 is well suited for welding blood vessels and many other tissues wherein collateral thermal damage is undesirable. However, it has been found that certain thin friable tissues, when welded under high compression as described above, can be susceptible to tearing or perforation along the line between the welded tissue and the non-welded tissue. For example, lung tissue can comprise the type of tissue that can be difficult to seal along a transected margin and where any leakage around the seal in is highly undesirable. In such cases, referring to FIG. 9, it can be desirable to selectively deliver Rf energy to the tissue to create a transition zone tz in which tissue is coagulated, but not necessarily welded, to add strength to the tissue across the tissue margin.

The working end 260 of FIG. 9 depicts guide members or jaws 205A and 205B that carry gradient electrode engagement surfaces 245A and 245B that cooperate with central electrode 215 to deliver bi-polar Rf current flow as described above. In this embodiment, the extension member 220 again is a non-conductive member that is used to create continuous high compression over the length of guide members 205A and 205B. The working end provides two features that are adapted to deliver Rf energy to collateral tissues et that can create a thermal transition zone tz of a selected dimension. First, the working end 260 provides electrode engagement surfaces 245A and 245B in the paired guide members that are non-parallel transverse to axis 265 of the openable-closable guide members 205A and 205B. Second, the working end provides gradient-type electrodes to induce current to flow progressively through selected adjacent portions of the engaged tissue. More in particular, still referring to FIG. 9, the electrode engagement surfaces 245A and 245B of the elongate guide members define first interior portions 266a–266b that are parallel (in transverse direction to axis 265) and are thus adapted for creating very high compressive forces on the captured tissue. The engagement surfaces 245A and 245B define second laterally-outward portions 270a-270 that are not parallel (transverse to axis 265) but provide an increasing dimension of gap g between the tissue engaging surfaces. The laterally increasing gap g between the electrode surfaces provides for Rf current flow that progressively creates a more effective weld in the direction of the center of the jaw structure. Further, the working end 260 and electrode engagement surfaces 245A and 245B provide the resistive gradients of resistant material 250 in adjacent portions 255a–255d of engagement surfaces as described in detail above. As depicted in FIG. 9, this combination of components is capable of first delivering Rf energy to the less compressed tissue volume in the transition zone tz, and then progressively inducing Rf current to flow between the bi-polar electrode arrangement by means of the resistive electrode portions 255a–255d similar to the manner shown in FIGS. 8A–8D.

Figure 10:
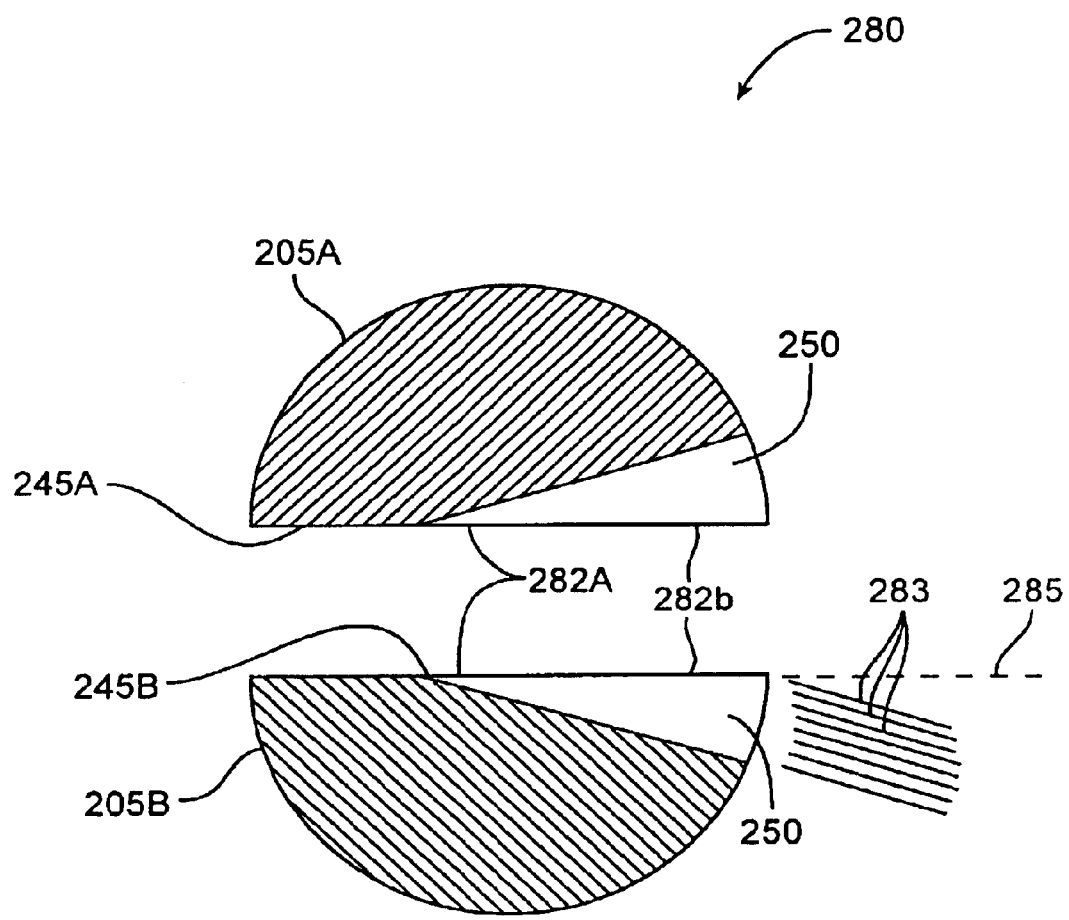
FIG. 10 depicts another embodiment of Type "B" working end with gradient electrodes in its engagement surfaces that have continuous tapered layers of resistive material across the engagement surfaces for progressively inducing Rf current flow through adjacent tissue portions.

FIG. 10 depicts the guide members or jaws 205A and 205B of another embodiment of working end 280 that carry gradient electrode engagement surfaces 245A and 245B. In this embodiment, the electrode surfaces have a tapered layer of resistive material 250 that provides a continuous and progressive resistive gradient across the engagement surfaces from thin portion 282a to thick portion 282b. One manner of making such an electrode engagement surface comprises the deposition of multiple thin layers 283 of resistive material on the surface of a member. Following such a build up of resistive material, a precision grinding process (along line 285) can be used to material at an angle to the build up to create the engagement surface as indicated in FIG. 10.

Figure 11:
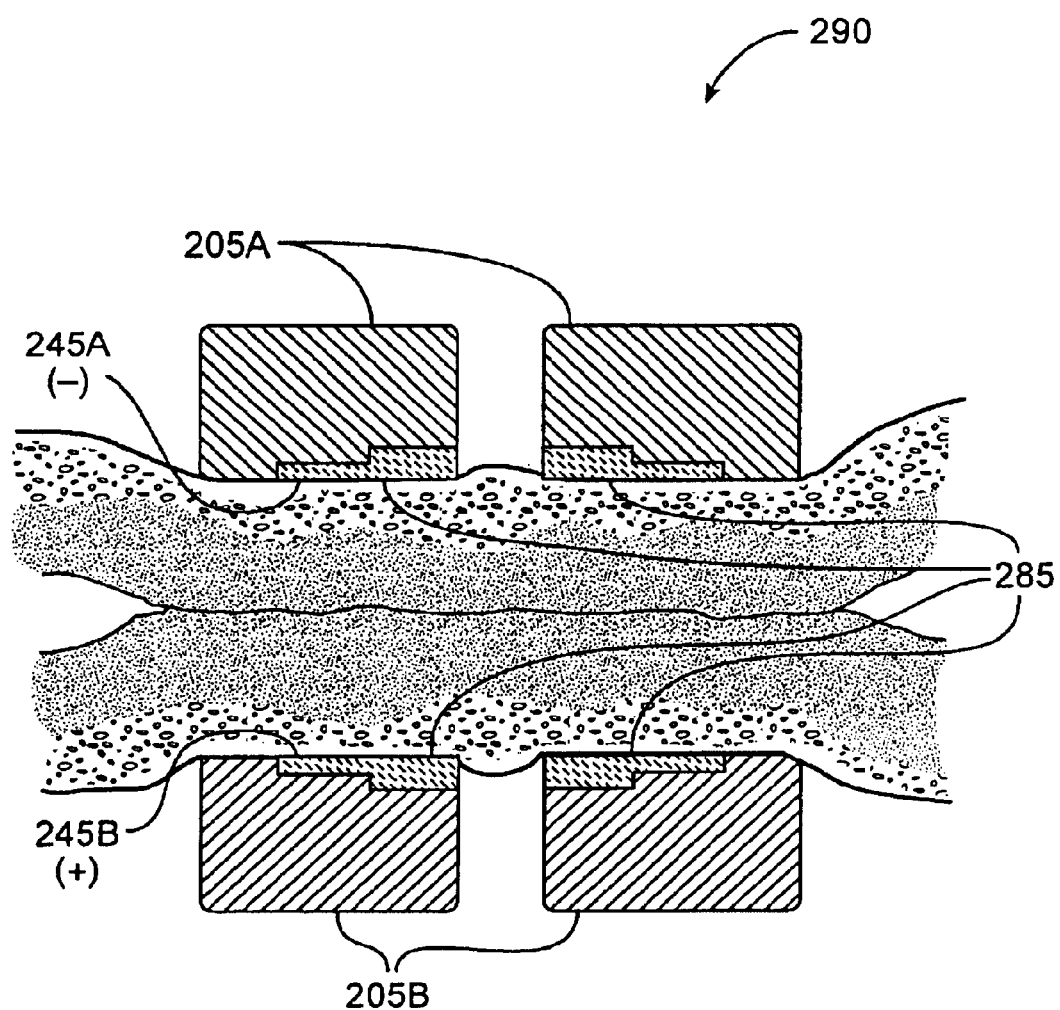
FIG. 11 depicts another embodiment of Type "B" working end with gradient electrodes that cooperate in first and second bi-polar jaws.

FIG. 11 depicts another embodiment of an electrosurgical working end 290 wherein the guide members or jaws 205A and 205B again carry gradient electrode surfaces 245A and 245B. In this embodiment, the gradient electrode engagement surfaces 245A and 245B themselves cooperate in a bi-polar electrode arrangement with surface 245A indicated with negative (−) polarity and surface 245B indicated with positive (+) polarity. Such opposing jaw surfaces can advantageously use gradient electrodes to progressively deliver Rf energy across the engagement surfaces, similar to the manner illustrated in FIGS. 8A–8D, but without the cooperation of a central electrode in contact with transected medial tissues. Such gradient electrodes in opposing jaw members also can be multiplexed in cooperation with a central electrode as described in U.S. Patent Applications listed above in the Section titled Cross-References to Related Applications, all of which are incorporated herein by reference.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. A working end of an electrosurgical instrument, comprising:

first and second engaging members carried at the distal end of an extension member, the engaging members capable of an open position and a closed position for engaging tissue; and first and second electrodes engagement surfaces exposed in faces of the engaging members, respectively, wherein an electrode surface defines a plurality of adjacent portions each having a different resistance to electrical current flow therethrough.

2. The working end of claim 1 wherein the first and second engaging members close about a central axis and wherein the adjacent portions with differential resistance extend parallel to said axis.

3. The working end of claim 2 wherein the said adjacent portions increase in resistance from portions further from said central axis toward portions closer to said central axis.

4. The working end of claim 1 wherein the first and second engaging members close about a central axis and wherein the adjacent portions with differential resistance extend transverse to said axis.

5. The working end of claim 1 wherein the first and second electrode surfaces have a common polarity.

6. The working end of claim 1 wherein the first and second electrodes have opposing polarities.

7. The working end of claim 1 wherein said differential resistance across an electrode engagement surface varies in a step-wise manner.

8. The working end of claim 1 wherein said differential resistance across an electrode engagement surface varies in a continuous manner.

9. The working end of claim 1 wherein said opposing first and second electrode engagement surfaces in the closed position are substantially parallel transverse to said central axis.

10. The working end of claim 1 wherein said opposing first and second electrode engagement surfaces in the closed position are substantially non-parallel transverse to said central axis.

11. The working end of claim 10 wherein said opposing first and second electrode engagement in the closed position define a gap therebetween that increases in dimension outwardly from said central axis.

12. A method of electrosurgically sealing a targeted tissue volume, comprising the steps of:

engaging the targeted tissue between opposing polarity electrode engagement surfaces, wherein at least one electrode engagement surface defines a plurality of electrode portion with differential resistance to electrical current flow therethrough;

causing Rf current flow through the engaged tissue between the opposing polarity electrodes;

wherein said Rf current flow is induced to flow progressively across different selected portions of the engaged tissue that are engaged by different electrode portions having differential resistance.

13. The method of claim 12 wherein the said Rf current flow is initially induced to flow through a selected tissue volume engaged by the electrode portion having the least resistance and thereafter progressively induced to flow through tissue volume engaged by electrode portions having greater resistance.

14. The method of claim 13 wherein the said Rf current flow is initially induced to flow through a tissue volume engaged by an electrode portion farthest outward from an axis of the engagement surfaces and thereafter progressively induced to flow through tissue volume engaged by electrode portions closer to said central axis.

15. The method of claim 12 wherein said opposing polarity electrode engagement surfaces engage opposing surface portions of the engaged tissue.

16. A method of directing the path of Rf current in a targeted tissue volume, comprising the steps of:

engaging the targeted tissue with a first electrode engagement surface that has at least two electrode portions with lesser and greater resistances to Rf current flow therethrough, and a second electrode coupled to tissue; and delivering Rf current to the first electrode engagement surface and the engaged tissue wherein said Rf current flow is first directed to flow in paths in tissue engaged by the electrode portion having lesser resistance and thereafter directed to flow in paths in tissue engaged by electrode portions having greater resistances.

17. The method of claim 16 wherein said first and second electrode engagement surfaces engage opposing outer surface portions of the targeted tissue volume.

18. The method of claim 16 wherein said first electrode engagement surface engages an outer surface portion of the engaged tissue and said second electrode comprises a ground electrode coupled to tissue.

* * * * *